United States Patent
Shimizu et al.

(10) Patent No.: US 10,584,197 B2
(45) Date of Patent: Mar. 10, 2020

(54) CROSSLINKING AGENT AND FLUORINE-CONTAINING AROMATIC COMPOUND

(71) Applicant: NICHIAS CORPORATION, Tokyo (JP)

(72) Inventors: Tomoya Shimizu, Tokyo (JP); Ayumi Maezawa, Tokyo (JP); Yuriko Sekimoto, Tokyo (JP)

(73) Assignee: NICHIAS CORPORATION, Tokyo (JP)

( * ) Notice: Subject to any disclaimer, the term of this patent is extended or adjusted under 35 U.S.C. 154(b) by 0 days.

(21) Appl. No.: 16/417,189

(22) Filed: May 20, 2019

(65) Prior Publication Data

US 2019/0270835 A1 Sep. 5, 2019

Related U.S. Application Data

(62) Division of application No. 15/501,146, filed as application No. PCT/JP2015/003888 on Jul. 31, 2015, now Pat. No. 10,344,113.

(51) Int. Cl.
| | |
|---|---|
| C07C 22/08 | (2006.01) |
| C07C 43/29 | (2006.01) |
| C08F 14/18 | (2006.01) |
| C08F 259/08 | (2006.01) |
| C08K 5/03 | (2006.01) |
| C08K 5/14 | (2006.01) |
| C08L 27/12 | (2006.01) |

(52) U.S. Cl.
CPC ........... *C08F 259/08* (2013.01); *C07C 22/08* (2013.01); *C07C 43/29* (2013.01); *C08F 14/18* (2013.01); *C08K 5/03* (2013.01); *C08K 5/14* (2013.01); *C08L 27/12* (2013.01)

(58) Field of Classification Search
CPC ........ C08F 259/08; C08F 14/18; C08L 27/12; C07C 22/08; C07C 43/29; C08K 5/03; C08K 5/14

See application file for complete search history.

(56) References Cited

U.S. PATENT DOCUMENTS

| | | | |
|---|---|---|---|
| 5,037,917 | A | 8/1991 | Babb et al. |
| 6,703,461 | B1 | 3/2004 | Tanaka et al. |
| 2003/0049399 | A1 | 3/2003 | Noguchi et al. |
| 2004/0147698 | A1 | 7/2004 | Tanaka et al. |
| 2004/0202891 | A1 | 10/2004 | Ishibashi et al. |
| 2005/0282969 | A1 | 12/2005 | Comino et al. |
| 2006/0051617 | A1 | 3/2006 | Ishibashi et al. |
| 2016/0032039 | A1 | 2/2016 | Shimizu et al. |
| 2016/0185892 | A1 | 6/2016 | Shimizu et al. |

FOREIGN PATENT DOCUMENTS

| | | |
|---|---|---|
| EP | 3031851 A1 | 6/2016 |
| JP | S55-79331 A | 6/1980 |
| JP | H11-199743 A | 7/1999 |
| JP | 2000-327846 A | 11/2000 |
| JP | 2006-009010 A | 1/2006 |
| JP | 2008-538651 A | 10/2008 |
| JP | 2009-242782 A | 10/2009 |
| JP | 2010119150 A | 5/2010 |
| JP | 2012-119150 A | 6/2012 |
| JP | 2012-211347 A | 11/2012 |
| WO | 98/36901 A1 | 8/1998 |
| WO | 99/50319 A1 | 10/1999 |
| WO | 2003/091357 A1 | 11/2003 |
| WO | 2006/113205 A2 | 10/2006 |

(Continued)

OTHER PUBLICATIONS

Shoji et al.; "Synthesis and FET characteristics of phenylene-vinylene and anthraracene-vinylene compounds containing cyano groups;" J. Mater. Chem.; 2010; pp. 6472-6478; vol. 20.

Saito et al.; "Highly Regioselective Cyclotrimerization of 1-Perfluoroalkyleneynes Catalyzed by Nickel;" J. Org. Chem.; 2001; pp. 796-802; vol. 66.

Davis et al.; "Stereoselective Preparation of (Z)-a, β-Difluorostyrenes;" Tetrahedron Letters; 1996; pp. 7237-7240; vol. 37, No. 40.

Davis et al.; "Stereoselective Preparation of (Z)-a, β-Difluorostyrenes and Stereospecific Conversion to (E)-a, β-Difluoro-β-iodostyrenes;" J. Org. Chem. 1997; pp. 9217-9222; vol. 62.

(Continued)

*Primary Examiner* — Irina S Zemel
*Assistant Examiner* — Jeffrey S Lenihan
(74) *Attorney, Agent, or Firm* — Oliff PLC

(57) ABSTRACT

A composition includes a fluoroelastomer, a crosslinking initiator, and a crosslinking agent. The crosslinking agent comprises a compound that comprises two or more structures represented by a formula (3),

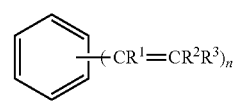

(3)

wherein $R^1$, $R^2$, and $R^3$ are independently a hydrogen atom, a fluorine atom, an alkyl group, a fluoroalkyl group, or a substituted or unsubstituted aryl group, a plurality of $R^1$ are identical to or different from each other, a plurality of $R^2$ are identical to or different from each other, a plurality of $R^3$ are identical to or different from each other, provided that at least one of $R^1$, $R^2$, and $R^3$ is a hydrogen atom, and at least one of $R^1$, $R^2$, and $R^3$ is a fluorine atom or a fluorine atom-containing group; n are independently an integer from 1 to 5; and each hydrogen on the benzene rings may be substituted.

8 Claims, No Drawings

(56) References Cited

FOREIGN PATENT DOCUMENTS

WO       2014/167797 A1    10/2014
WO       2015/019581 A1    2/2015

OTHER PUBLICATIONS

Glowatzki et al.; "Band Gap Tunable N-Type Molecules for Organic Field Effect Transistors;" J. Phys. Chem. C; 2013; pp. 11530-11539; vol. 117.
Raghavanpillai et al.; "Room Temperature Preparation of Trifluoroethenylzinc Reagent by Metalation of the Readily Available Halocarbon HFC-134a and an Efficient, Economically Viable Synthesis of 1,2,2-Trifluorostyrenes;" J. Org. Chem.; 2004; pp. 7083-7091; vol. 69.
Oct. 13, 2015 Search Report issued in International Application No. PCT/JP2015/003888.
Oct. 13, 2015 Written Opinion of the International Searching Authority issued in International Application No. PCT/JP2015/003888.
Feb. 23, 2018 Office Action issued in European Patent Application No. 15826584.3.
May 24, 2018 Office Action issued in Chinese Patent Application No. 201580041357.7.
Prakash "A Domino Approach of Heck Coupling for the Synthesis of Beta-Trifluoromethylstyrenes" Organic Letters, 2012, vol. 14, pp. 1146-1149, 2012.
Kvicala "Experimental and theoretical study of Hoveyda-Grubbs Catalysts modified by perfluorohexyl ponytail in the alkoxybenzylidene ligand," Journal of Fluorine Chemistry, vol. 153, pp. 12-25, 2013.
Dec. 26, 2019 Office Action issued U.S. Appl. No. 16/255,276.
Kubota et al., "1,1-Difluoro-1-alkenes as new electrolyte additives for lithium ion batteries," Journal of Power Sources, 2012, 207, pp. 141-149.

CROSSLINKING AGENT AND FLUORINE-CONTAINING AROMATIC COMPOUND

RELATED APPLICATION

The present application is a divisional application of U.S. application Ser. No. 15/501,146 filed Feb. 1, 2017, which in turn is a U.S. national stage application of PCT/JP2015/003888 filed Jul. 31, 2015. The disclosure of each of these prior applications is incorporated herein by reference in its entirety.

TECHNICAL FIELD

The invention relates to a crosslinking agent, a composition that includes a crosslinking agent, a crosslinked fluoroelastomer, a formed article obtained by using a crosslinked fluoroelastomer, and a fluorine-containing aromatic compound.

BACKGROUND ART

Water vapor (steam) is used in various industries (e.g., plant industry, machine (mechanical) industry, food industry, and medical industry) for power generation, sterilization, cleaning (washing), and the like. A seal material (e.g., rubber O-ring) is used for a pipe and a device in which water vapor flows, and prevents water vapor from flowing to the outside.

In recent years, there has been a tendency that the temperature of water vapor used in power plants is increased in order to improve the power generation efficiency. Therefore, high-temperature water vapor resistance has been desired for a seal material. In such a case, a seal material formed of a crosslinked fluoroelastomer (e.g., fluororubber or perfluororubber) is used. However, a seal material formed of a crosslinked fluoroelastomer may exhibit poor vapor resistance, and a further improvement has been desired (see Patent Literature 1, for example).

A crosslinking agent is used when producing a crosslinked fluoroelastomer, and various crosslinking agents have been known. For example, triallyl isocyanurate (TAIC) is generally widely known (see Patent Literature 2 to 6, for example), and divinylbenzene (see Patent Literature 2 to 5, for example), divinylbiphenyl (see Patent Literature 5, for example), and the like are also known.

However, a novel crosslinking agent that can further improve the heat resistance and the vapor resistance of a crosslinked fluoroelastomer has been desired.

Patent Literature 6 discloses tetrafluoroethylene and a perfluoroalkyl vinyl ether as a raw material monomer for producing a fluoroelastomer.

Non-Patent Literature 1 discloses 1,2,2-trifluorostyrene (perfluorovinylbenzene) as a material for producing a fuel cell separation membrane.

CITATION LIST

Patent Literature

Patent Literature 1: JP-A-2006-9010
Patent Literature 2: JP-A-2009-242782
Patent Literature 3: JP-A-H11-199743
Patent Literature 4: WO1998/036901
Patent Literature 5: JP-A-2000-327846
Patent Literature 6: JP-A-2012-211347

Non-Patent Literature

Non-Patent Literature 1: A. Raghavanpillai, et al., J. Org. Chem., 2004, vol. 69, pp. 7083-7091

SUMMARY OF INVENTION

The invention was conceived in view of the above problems. An object of the invention is to provide a crosslinking agent that can improve the heat resistance of a crosslinked fluoroelastomer, and a crosslinked fluoroelastomer that exhibits improved heat resistance.

Another object of the invention is to provide a novel fluorine-containing aromatic compound that can be used as a crosslinking agent.

The invention provides the following crosslinking agent, crosslinked fluoroelastomer, fluorine-containing aromatic compound, and the like.

1. A crosslinking agent including a compound represented by a formula (1),

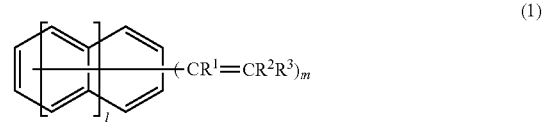

wherein $R^1$, $R^2$, and $R^3$ are independently a hydrogen atom, a fluorine atom, an alkyl group, a fluoroalkyl group, or a substituted or unsubstituted aryl group, a plurality of $R^1$ are identical to or different from each other, a plurality of $R^2$ are identical to or different from each other, a plurality of $R^3$ are identical to or different from each other, provided that at least one of $R^1$, $R^2$, and $R^3$ is a hydrogen atom, and at least one of $R^1$, $R^2$, and $R^3$ is a fluorine atom or a fluorine atom-containing group, m is an integer from 2 to 6, l is an integer from 0 to 2, and each hydrogen on the benzene ring(s) may be substituted.

2. The crosslinking agent according to 1, wherein the compound represented by the formula (1) is a compound represented by a formula (2),

wherein $R^1$, $R^2$, $R^3$, and m are the same as defined above in connection with the formula (1), and each hydrogen on the benzene ring may be substituted.

3. A crosslinking agent including a compound that includes two or more structures represented by a formula (3),

wherein $R^1$, $R^2$, and $R^3$ are independently a hydrogen atom, a fluorine atom, an alkyl group, a fluoroalkyl group, or a substituted or unsubstituted aryl group, a plurality of $R^1$ are identical to or different from each other, a plurality of $R^2$ are identical to or different from each other, a plurality of $R^3$ are identical to or different from each other, provided that at least one of $R^1$, $R^2$, and $R^3$ is a hydrogen atom, and at least one of $R^1$, $R^2$, and $R^3$ is a fluorine atom or a fluorine atom-containing group, n are independently an integer from 1 to 5, and each hydrogen on the benzene rings may be substituted.

4. The crosslinking agent according to 3, wherein the compound that includes two or more structures represented by the formula (3) is a compound represented by a formula (4),

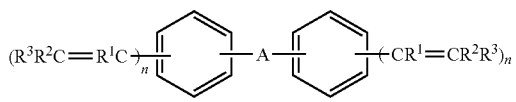

(4)

wherein A is a single bond, —O—, —S—, a heteroatom-containing group, a linear or a branched alkylene group, a cycloalkylene group, or an arylene group that may be fluorinated partially or completely, $R^1$, $R^2$, $R^3$, and n are the same as defined above in connection with the formula (3), and each hydrogen on the benzene rings may be substituted.

5. The crosslinking agent according to 1 or 3, wherein the compound represented by the formula (1), or the compound that includes two or more structures represented by the formula (3), is a compound represented by a formula (5),

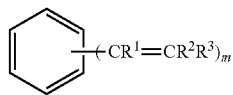

(5)

wherein $R^1$, $R^2$, and $R^3$ are the same as defined above in connection with the formula (1) or (3), o is 1 or 0, q are independently an integer from 1 to 4, and each hydrogen on the benzene rings may be substituted.

6. The crosslinking agent according to any one of 1 to 5, wherein $R^1$, $R^2$, and $R^3$ are independently a hydrogen atom, a fluorine atom, an alkyl group, a fluoroalkyl group, or a substituted or unsubstituted phenyl or naphthyl group.

7. A composition including a fluoroelastomer, a crosslinking initiator, and the crosslinking agent according to any one of 1 to 6.

8. The composition according to 7, wherein the fluoroelastomer is a perfluoroelastomer or a partially fluorinated elastomer.

9. The composition according to 7 or 8, including the crosslinking agent in an amount of 0.5 to 30 mmol based on 100 g of the fluoroelastomer.

10. The composition according to any one of 7 to 9, including the crosslinking initiator in an amount of 0.3 to 15 mmol based on 100 g of the fluoroelastomer.

11. A crosslinked fluoroelastomer obtained by crosslinking the composition according to any one of 7 to 10.

12. A formed article including the crosslinked fluoroelastomer according to 11.

13. The formed article according to 12, the formed article being a seal material.

14. A compound represented by a formula (1),

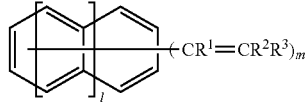

(1)

wherein $R^1$, $R^2$, and $R^3$ are independently a hydrogen atom, a fluorine atom, an alkyl group, a fluoroalkyl group, or a substituted or unsubstituted aryl group, a plurality of $R^1$ are identical to or different from each other, a plurality of $R^2$ are identical to or different from each other, a plurality of $R^3$ are identical to or different from each other, provided that at least one of $R^1$, $R^2$, and $R^3$ is a hydrogen atom, and at least one of $R^1$, $R^2$, and $R^3$ is a fluorine atom or a fluorine atom-containing group, m is an integer from 2 to 6, l is an integer from 0 to 2, and each hydrogen on the benzene ring(s) may be substituted.

15. The compound according to 14, the compound being represented by a formula (2),

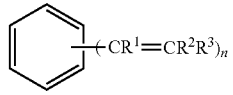

(2)

wherein $R^1$, $R^2$, $R^3$, and m are the same as defined above in connection with the formula (1), and each hydrogen on the benzene ring may be substituted.

16. A compound including two or more structures represented by a formula (3),

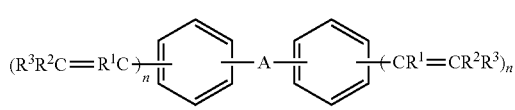

(3)

wherein $R^1$, $R^2$, and $R^3$ are independently a hydrogen atom, a fluorine atom, an alkyl group, a fluoroalkyl group, or a substituted or unsubstituted aryl group, a plurality of $R^1$ are identical to or different from each other, a plurality of $R^2$ are identical to or different from each other, a plurality of $R^3$ are identical to or different from each other, provided that at least one of $R^1$, $R^2$, and $R^3$ is a hydrogen atom, and at least one of $R^1$, $R^2$, and $R^3$ is a fluorine atom or a fluorine atom-containing group, n are independently an integer from 1 to 5, and each hydrogen on the benzene rings may be substituted.

17. The compound according to 16, the compound being represented by a formula (4), (4)

wherein A is a single bond, —O—, —S—, a heteroatom-containing group, a linear or a branched alkylene group, a cycloalkylene group, or an arylene group that may be fluorinated partially or completely, $R^1$, $R^2$, $R^3$, and n are the same as defined above in connection with the formula (3), and each hydrogen on the benzene rings may be substituted.
18. The compound according to 14 or 16, the compound being represented by a formula (5),

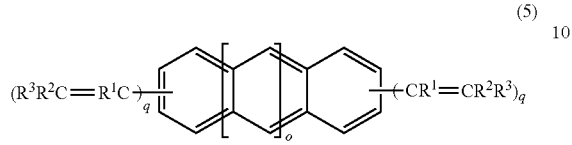

wherein $R^1$, $R^2$, and $R^3$ are the same as defined above in connection with the formula (1) or (3), o is 1 or 0, q are independently an integer from 1 to 4, and each hydrogen on the benzene rings may be substituted.
19. A crosslinked fluoroelastomer having a change ratio of 70% or less with respect to a weight swelling ratio when exposed to saturated water vapor at 300° C. for 22 hours, the weight swelling ratio being measured after immersing the crosslinked fluoroelastomer in a perfluorocarbon solution at 21 to 25° C. for 72 hours.
20. A crosslinked fluoroelastomer having a weight reduction ratio of 7% or less when exposed to an atmospheric environment at 330° C. for 16 hours.

The invention also provides the following compounds.
i. Compounds respectively represented by the following formulas.

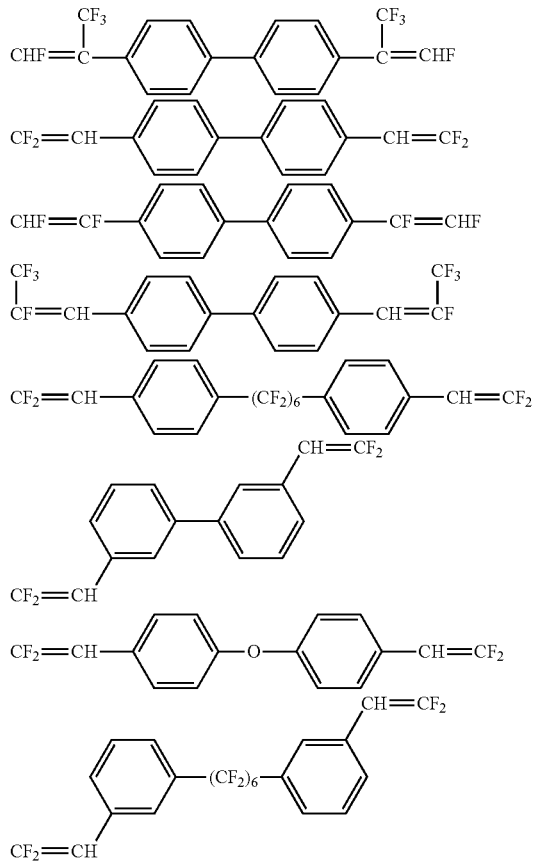

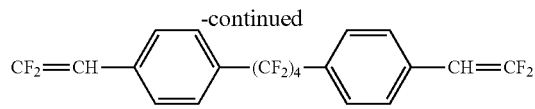

ii. A compound including two or more structures represented by a formula (3'),

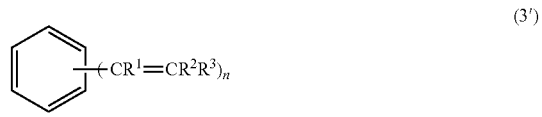

wherein $R^1$, $R^2$, and $R^3$ are independently a hydrogen atom, a fluorine atom, an alkyl group, a fluoroalkyl group, or a substituted or unsubstituted aryl group, a plurality of $R^1$ are identical to or different from each other, a plurality of $R^2$ are identical to or different from each other, a plurality of $R^3$ are identical to or different from each other, provided that at least one of $R^1$, $R^2$, and $R^3$ is a hydrogen atom, and at least one of $R^1$, $R^2$, and $R^3$ is a fluorine atom or a fluorine atom-containing group, n are independently an integer from 1 to 5, and each hydrogen on the benzene rings may be substituted, provided that the following compounds are excluded.

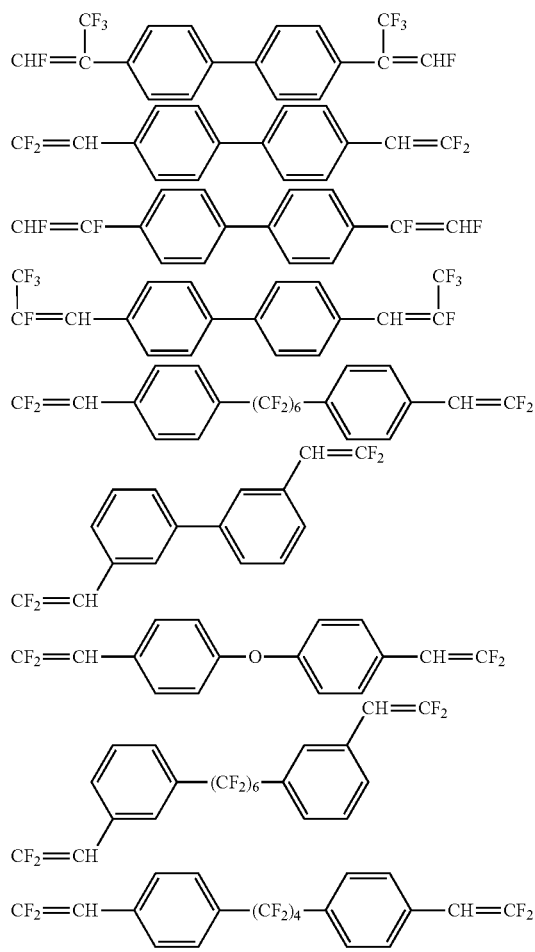

iii. The compound according to ii, the compound being represented by a formula (4'),

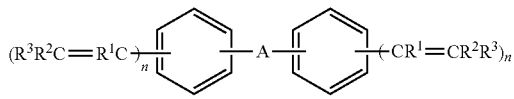
(4')

wherein A is a single bond, —O—, —S—, a heteroatom-containing group, a linear or a branched alkylene group, a cycloalkylene group, or an arylene group and these groups may be fluorinated partially or completely, $R^1$, $R^2$, $R^3$, and n are the same as defined above in connection with the formula (3), and each hydrogen on the benzene rings may be substituted.

The invention thus provides a crosslinking agent that can improve the heat resistance of a crosslinked fluoroelastomer, and a crosslinked fluoroelastomer that exhibits improved heat resistance.

The invention thus also provides a novel fluorine-containing aromatic compound that can be used as a crosslinking agent.

DESCRIPTION OF EMBODIMENTS

An embodiment of the invention is described below. Note that the invention is not limited to the following embodiment.

A crosslinking agent according to one embodiment of the invention is a compound represented by the following formula (1).

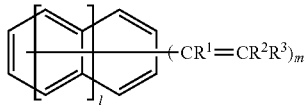
(1)

$R^1$, $R^2$, and $R^3$ in the formula (1) are independently a hydrogen atom, a fluorine atom, an alkyl group, a fluoroalkyl group, or a substituted or unsubstituted aryl group. At least one of $R^1$, $R^2$, and $R^3$ is a hydrogen atom, and at least one of $R^1$, $R^2$, and $R^3$ that are not a hydrogen atom is a fluorine atom or a fluorine atom-containing group. Examples of the fluorine atom-containing group include a fluoroalkyl group, and an aryl group that is substituted with a fluorine atom or a fluoroalkyl group.

The alkyl group and the alkyl residue included in the fluoroalkyl group may be linear or branched. The number of carbon atoms included in the alkyl is preferably 1 to 15 (more preferably 1 to 6).

The fluoroalkyl group has a structure in which the alkyl group is fluorinated partially or completely. The fluoroalkyl group is preferably a perfluoroalkyl group.

The number of carbon atoms included in the aryl group is preferably 6 to 18 (more preferably 6 to 12). Examples of the aryl group include a phenyl group, a naphthyl group, and the like.

Examples of a substituent that may substitute the aryl group include a fluorine atom, a linear or branched alkyl group, a cycloalkyl group, an aryl group, and the like. These groups may be fluorinated partially or completely. The number of carbon atoms included in the linear or branched alkyl group is preferably 1 to 15 (more preferably 1 to 6). The number of carbon atoms included in the cycloalkyl group is preferably 3 to 8 (more preferably 3 to 6). The number of carbon atoms included in the aryl group is preferably 6 to 18 (more preferably 6 to 12).

It is preferable that $R^1$, $R^2$, and $R^3$ be independently a hydrogen atom, a fluorine atom, an alkyl group, or a fluoroalkyl group.

Examples of the group represented by —$CR^1$=$CR^2R^3$ (fluorine-containing substituted vinyl group) include the following groups. The m groups represented by —$CR^1$=$CR^2R^3$ may be identical to or different from each other.

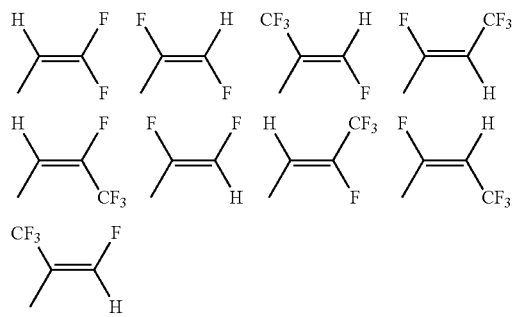

m in the formula (1) is 2, 3, 4, 5, or 6, and preferably 2.

l in the formula (1) is 0, 1, or 2. l is preferably 0.

Examples of the compound represented by the formula (1) include compounds respectively represented by the following formulas (2), (6), and (7).

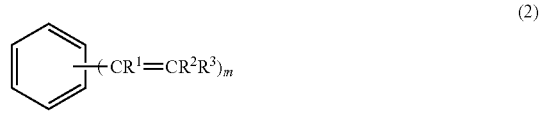
(2)

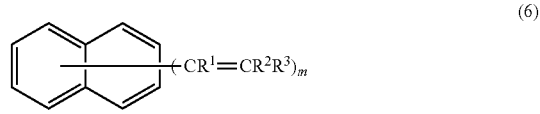
(6)

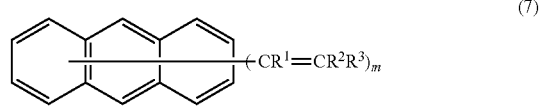
(7)

$R^1$, $R^2$, $R^3$, and m in the formulas (2), (6), and (7) are the same as defined above.

When m in the formula (2) is 2, the two groups represented by —$CR^1$=$CR^2R^3$ may be situated at ortho positions, meta positions, or para positions. It is preferable that the two groups represented by —$CR^1$=$CR^2R^3$ be situated at para positions.

A crosslinking agent according to another embodiment of the invention is a compound that includes two or more structures represented by the following formula (3). The benzene ring included in the formula (3) may be bonded to another group or ring, and may be fused with another ring.

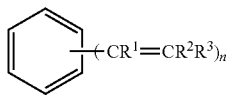
(3)

$R^1$, $R^2$, and $R^3$ in the formula (3) are the same as defined above in connection with the formula (1). n are independently 1, 2, 3, 4, or 5.

Examples of a preferable compound that includes two or more structures represented by the formula (3) include a compound represented by the following formula (4).

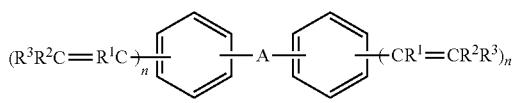
(4)

A in the formula (4) is a single bond, —O—, —S—, a heteroatom-containing group, a linear or a branched alkylene group, a cycloalkylene group, or an arylene group that is optionally fluorinated partially or completely. For example, the alkylene group, the cycloalkylene group, and the arylene group are optionally fluorinated.

The number of carbon atoms included in the linear or a branched alkylene group is preferably 1 to 15 (more preferably 1 to 6). The number of carbon atoms included in the cycloalkylene group is preferably 3 to 8 (more preferably 3 to 6). The number of carbon atoms included in the arylene group is preferably 6 to 18 (more preferably 6 to 12).

Examples of the alkylene group include a methylene group, an ethylene group, a propylene group, and the like. Examples of the arylene group include a phenylene group, a naphthalenylene group, and the like.

$R^1$, $R^2$, $R^3$, and n in the formula (4) are the same as defined above.

When each n in the formula (4) is 1, A and the group represented by —$CR^1$=$CR^2R^3$ may be situated at ortho positions, meta positions, or para positions. It is preferable that A and the group represented by —$CR^1$=$CR^2R^3$ be situated at para positions. It is more preferable that A and the group represented by —$CR^1$=$CR^2R^3$ be situated at para positions with respect to each benzene ring.

Specific examples of the compound represented by the formula (4) include compounds respectively represented by the following formulas (8) to (10).

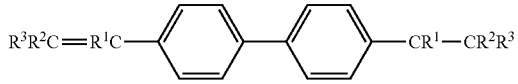
(8)

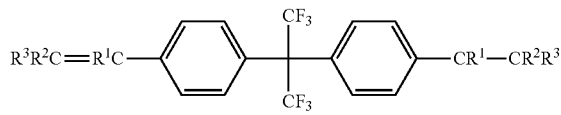
(9)

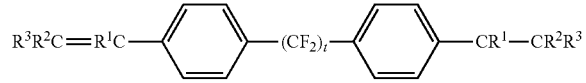
(10)

$R^1$, $R^2$, and $R^3$ in the formulas (8) to (10) are the same as defined above. t in the formula (10) is preferably 1 to 15, and more preferably 1 to 6.

Specific examples of the compound represented by the formula (3) include the following compounds (crosslinking agents).

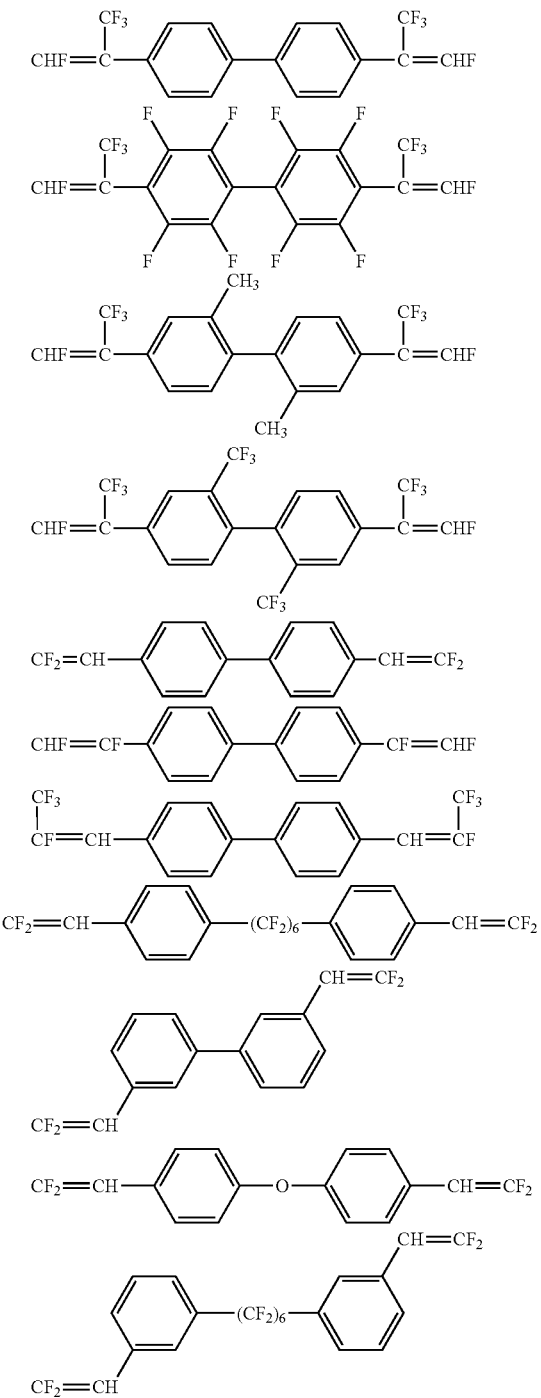

Examples of the compound represented by the formula (1), or the compound that includes two or more structures represented by the formula (3) include a compound represented by the following formula (5).

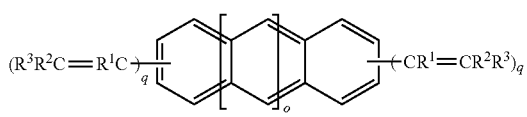

(5)

$R^1$, $R^2$, and $R^3$ in the formula (5) are the same as defined above.

o in the formula (5) is 1 or 0, and preferably 0.

q in the formula (5) are independently 1, 2, 3, or 4.

Specific examples of the compound represented by the formula (5) include a compound represented by the following formula (11) and a compound represented by the following formula (12).

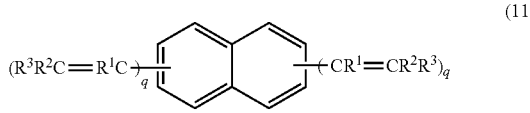

(11)

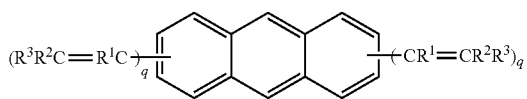

(12)

$R^1$, $R^2$, $R^3$, and q in the formulas (11) and (12) are the same as defined above.

When each q in the formulas (11) and (12) is 1, it is possible to effect efficient crosslinking if the two groups represented by $-CR^1=CR^2R^3$ are situated farthest from each other.

Each hydrogen on the benzene ring(s) included in the formulas (1) to (12) may be independently substituted with a substituent. The term "hydrogen on the benzene ring(s)" used herein refers to a hydrogen atom included in a benzene skeleton, a naphthalene skeleton, or an anthracene skeleton. Examples of the substituent include a fluorine atom, an alkyl group, a fluoroalkyl group, a cycloalkyl group, a fluorocycloalkyl group, a substituted or unsubstituted aryl group, and the like. The fluoroalkyl group and the fluorocycloalkyl group have a structure in which the alkyl group or the cycloalkyl group is fluorinated partially or completely.

The alkyl group may be linear or branched. The number of carbon atoms included in the alkyl group is preferably 1 to 15 (more preferably 1 to 6). The number of carbon atoms included in the cycloalkyl group is preferably 3 to 8 (more preferably 3 to 6). The number of carbon atoms included in the aryl group is preferably 6 to 18 (more preferably 6 to 12). Examples of a substituent that may substitute the aryl group include those mentioned above in connection with $R^1$.

Examples of the alkyl group include a methyl group, an ethyl group, a propyl group, and the like. Examples of the arylene group include a phenylene group, a naphthalenylene group, and the like.

A composition according to the invention includes the above crosslinking agent, a fluoroelastomer, and an initiator.

The crosslinking agent is preferably added in an amount of 0.5 to 30 mmol, more preferably 0.5 to 15 mmol, still more preferably 1 to 13 mmol, even more preferably 1 to 8 mmol, and yet more preferably 2.0 to 7.0 mmol, based on 100 g of the fluoroelastomer. There is a tendency that vapor resistance and heat resistance are improved as the amount of crosslinking agent increases. However, the composition may become hard if the amount of crosslinking agent is too large.

The fluoroelastomer may be a perfluoroelastomer, or may be a partially fluorinated elastomer.

For example, the fluoroelastomer may include a repeating unit derived from the monomers listed below. The fluoroelastomer may include one or two or more repeating units derived from one or two or more monomers.

$CF_2=CH_2$ (vinylidene fluoride)
$CF_2=CF_2$ (tetrafluoroethylene)
$CF_2=CFCF_3$ (hexafluoropropylene)
$CH_2=CH_2$
$CH_2=CHCH_3$ The fluoroelastomer used in connection with the invention preferably includes either or both of iodine and bromine (more preferably iodine) as a radical attack site during crosslinking (curing). A perfluoroelastomer that can be cured using a peroxide is disclosed in Patent Literature 1, for example.

A (per)fluoroelastomer normally includes iodine in an amount of 0.001 to 5 wt %, and preferably 0.01 to 2.5 wt %, based on the total weight of the polymer. The iodine atoms may be present along the chain, or may be present at the terminal, or may be present along the chain and at the terminal.

The (per)fluoroelastomer is produced from a copolymer of a (per)fluoroolefin or the like that includes one ethylenically unsaturated bond (preferably at the terminal).

Examples of the comonomer include the following compounds:

$CF_2=CFOR_{2f}$ ((per)fluoroalkyl vinyl ether (PAVE))

wherein $R_{2f}$ is a (per)fluoroalkyl group having 1 to 6 carbon atoms, such as a trifluoromethyl group or a pentafluoropropyl group;

$CF_2=CFOX_0$ ((per)fluorooxyalkyl vinyl ether)

wherein $X_0$ is a (per)fluorooxyalkyl group having 1 to 12 carbon atoms that includes one or more ether groups, such as a perfluoro-2-propoxypropyl group; and $CFX_2=CX_2OCF_2OR''_f$ (I-B)

wherein $R''_f$ is a linear or branched (per)fluoroalkyl group having 2 to 6 carbon atoms, a cyclic (per)fluoroalkyl group having 5 or 6 carbon atoms, or a linear or branched (per)fluorooxyalkyl group having 2 to 6 carbon atoms that includes 1 to 3 oxygen atoms, and $X_2$ is F or H.

The (per)fluorovinyl ether represented by the formula (I-B) is preferably represented by the following formula.

$CFX_2=CX_2OCF_2OCF_2CF_2Y$ (II-B)

wherein Y is F or $OCF_3$, and $X_2$ is the same as defined above.

The perfluorovinyl ethers represented by the following formulas are more preferable.

$CF_2=CFOCF_2OCF_2CF_3$ (MOVE1)

$CF_2=CFOCF_2OCF_2CF_2OCF_3$ (MOVE2)

Examples of a preferable monomer composition include the following compositions.
Tetrafluoroethylene (TFE): 50 to 85 mol %, PAVE: 15 to 50 mol %
TFE: 50 to 85 mol %, MOVE: 15 to 50 mol %

The fluoroelastomer may also include a unit derived from vinylidene fluoride, a fluoroolefin having 3 to 8 carbon atoms that may include either or both of chlorine and bromine, and a non-fluorinated olefin having 3 to 8 carbon atoms.

A common crosslinking initiator may be used. Examples of the crosslinking initiator include a peroxide, an azo compound, and the like.

The crosslinking initiator is preferably added in an amount of 0.3 to 35 mmol, more preferably 1 to 15 mmol, and still more preferably 1.5 to 10 mmol, based on 100 g of the fluoroelastomer. There is a tendency that vapor resistance and heat resistance are improved as the amount of crosslinking initiator increases. Scorching or foaming may occur if the amount of crosslinking initiator is too large.

The composition may include a crosslinking assistant.

Examples of the crosslinking assistant include zinc oxide, activated alumina, magnesium oxide, a quaternary ammonium salt, a quaternary phosphonium salt, an amine, and the like. The crosslinking assistant improves crosslinking efficiency and heat resistance. The crosslinking assistant is normally added in an amount of 0.1 to 10 g based on 100 g of the fluoroelastomer.

A filler can be added to the above fluoroelastomer composition in order to improve mechanical strength. A material that is commonly known as a filler for an elastomer may be used as the filler as long as the advantageous effects of the invention are not impaired. Examples of the filler include carbon black, silica, barium sulfate, titanium dioxide, a semicrystalline fluoropolymer, a perfluoropolymer, and the like.

An appropriate amount of a thickener, a pigment, a coupling agent, an antioxidant, a stabilizer, or the like may optionally be added to the composition.

A crosslinked fluoroelastomer can be obtained by crosslinking the composition according to the invention.

When using a one-step heating process, the composition is preferably crosslinked by heating the composition at 100 to 250° C. for 10 minutes to 5 hours.

When using a two-step heating process, the raw material is normally put in a die, and crosslinked with pressing (primary crosslinking). For example, primary crosslinking is effected by heating the raw material at 150 to 200° C. for 5 to 60 minutes. The resulting crosslinked product is removed from the die, and subjected to secondary crosslinking. For example, secondary crosslinking is effected by heating the crosslinked product at 150 to 300° C. for 1 to 100 hours. The crosslinking process may be performed using an electric furnace or the like. It is possible to suppress deformation and the like during use by providing a heat history through secondary crosslinking.

The crosslinking process may be performed in an inert gas atmosphere or air.

Nitrogen, helium, argon, or the like may be used as the inert gas. It is preferable to use nitrogen. The oxygen concentration in the inert gas atmosphere is preferably 10 ppm or less, and more preferably 5 ppm or less.

The crosslinked fluoroelastomer obtained using the above production method may be used as a seal material. The crosslinked fluoroelastomer may be formed in the shape of a gasket, a seal ring, or the like.

The above production method can produce a formed article that has a weight swelling change ratio (change ratio with respect to weight swelling ratio) of 70% or less before and after being exposed to saturated water vapor at 300° C. for 22 hours (as measured using the method described later in connection with the examples). The weight swelling change ratio is preferably 65% or less, and more preferably 55% or less.

The crosslinked fluoroelastomer (formed article) preferably has a weight reduction ratio (i.e., heat resistance) of 7% or less, and more preferably 5% or less, before and after being exposed to an atmospheric environment at 330° C. for 16 hours.

EXAMPLES

Example 1

Synthesis of Compound 1

A compound 1 was synthesized as described below.

A 500 mL four-necked flask equipped with a stirrer was charged with 4,4'-dibromobiphenyl (5.85 g, 18.8 mmol) and tetrahydrofuran (200 mL) in a nitrogen atmosphere. A solution prepared by dissolving n-butyllithium in n-hexane (1.6 M, 25.8 mL, 41.3 mmol) was slowly added dropwise to the mixture at −78° C. with stirring. Next, ethyl trifluoroacetate (11.73 g, 82.5 mmol) was slowly added dropwise to the mixture. After heating the resulting mixture to 0° C., a hydrochloric acid aqueous solution was added to the mixture, and the organic layer was isolated and removed. The organic layer was washed with a 20% sodium chloride solution (50 mL, 3 times), dried over anhydrous magnesium sulfate, and concentrated under reduced pressure. The resulting concentrate was washed with hexane to obtain 6.17 g of 4,4'-bis(trifluoroacetyl)biphenyl (light yellow solid).

A 300 mL four-necked flask equipped with a stirrer was charged with triphenylphosphine (26.5 g, 101.0 mmol) and tetrahydrofuran (40 mL) in a nitrogen atmosphere. A solution (20 mL) prepared by dissolving fluorotribromomethane (19.2 g, 70.9 mmol) in tetrahydrofuran was slowly added dropwise to the mixture at 0° C. with stirring. Next, a solution (40 mL) prepared by dissolving 4,4'-bis(trifluoroacetyl)biphenyl (6.13 g, 17.7 mmol) in tetrahydrofuran was added dropwise to the mixture, and the resulting mixture was stirred at room temperature for 5 hours. After the addition of hexane (100 mL), a solid precipitate was separated by filtration. The filtrate was washed with a 20% sodium chloride solution (100 mL, 3 times), dried over anhydrous magnesium sulfate, and concentrated under reduced pressure. The resulting concentrate was purified by silica gel chromatography to obtain 7.30 g of 4,4'-bis(1-trifluoromethyl-2-fluoro-2-bromovinyl)biphenyl (yellow solid).

A 300 mL four-necked flask equipped with a stirrer was charged with 4,4'-bis(1-trifluoromethyl-2-fluoro-2-bromovinyl)biphenyl (6.23 g, 11.6 mmol) and tetrahydrofuran (120 mL) in a nitrogen atmosphere. A solution prepared by dissolving n-butyllithium in n-hexane (1.6 M, 15.7 mL, 25.1 mmol) was added dropwise to the mixture at −78 to −55° C. with stirring. After the addition of water (3.0 g), the mixture was heated to room temperature. The organic layer was washed with a 20% sodium chloride solution (20 mL, 3 times), dried over anhydrous magnesium sulfate, and concentrated under reduced pressure. The resulting concentrate was purified by silica gel chromatography to obtain 1.10 g of 4,4'-bis(1-trifluoromethyl-2-fluorovinyl)biphenyl (compound 1) (light yellow oil) (isolated yield: 15%).

(Compound 1)

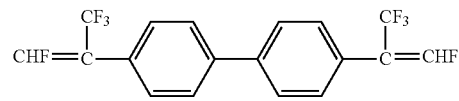

The compound 1 was liquid at room temperature.

The compound 1 was subjected to GC-MS, ¹H-NMR, and ¹⁹F-NMR analysis. The results are listed below. It was found that the compound 1 was a mixture including three isomers (E-E, E-Z, and Z-Z). The ratio (E-E:E-Z:Z-Z) of these isomers was 29:53:18.

The devices used for the analysis are listed below.
GC-MS: GCMS-QP2010 Plus manufactured by Shimadzu Corporation
¹H-NMR and ¹⁹F-NMR: AVANCE II 400 manufactured by BRUKER
GC-MS (m/z): 377 (M⁺-1), 358, 338, 309, 287, 269, 238, 220, 189

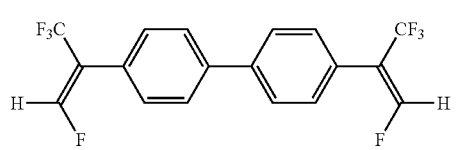
[E-E]

¹H-NMR (Acetone-d₆, 400 MHz); 7.37 ppm (d, 2H), 7.52-7.57 ppm (m, 4H, Ar—H), 7.79-7.85 ppm (m, 4H, Ar—H)
¹⁹F-NMR (Acetone-d₆, 376 MHz); −111.1 ppm (ddd, 2F), −57.6 ppm (d, 6F, CF₃)

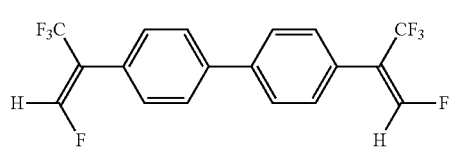
(E-Z)

¹H-NMR (Acetone-d₆, 400 MHz); 7.37 ppm (d, 1H), 7.52-7.57 ppm (m, 4H, Ar—H), 7.70 ppm (d, 1H), 7.79-7.85 ppm (m, 4H, Ar—H)
¹⁹F-NMR (Acetone-d₆, 376 MHz); −121.9 ppm (ddd, 1F), −111.1 ppm (ddd, 1F), −61.6 ppm (d, 3F, CF₃), −57.6 ppm (d, 3F, CF₃)

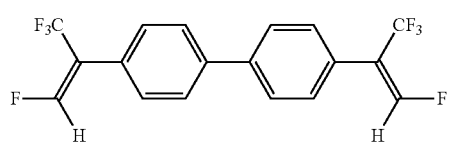
(Z-Z)

¹H-NMR (Acetone-d₆, 400 MHz); 7.52-7.57 ppm (m, 4H, Ar—H), 7.70 ppm (d, 2H), 7.79-7.85 ppm (m, 4H, Ar—H)
¹⁹F-NMR (Acetone-d₆, 376 MHz); −121.9 ppm (ddd, 2F), −61.6 ppm (d, 6F, CF₃)

Evaluation of Compound 1

A composition was prepared by mixing the components listed below.
Fluoroelastomer (Tecnoflon PFR 94 manufactured by Solvay): 100 g
Acid acceptor (AEROSIL R 972 manufactured by Nippon Aerosil Co., Ltd.): 1.0 g
Initiator (PERCUMYL D manufactured by NOF Corporation): 2.6 mmol
Crosslinking agent (compound 1): 6.1 mmol The composition was crosslinked to produce a crosslinked fluoroelastomer (formed article). Primary crosslinking was effected at 190° C. for 30 minutes, and secondary crosslinking was effected at 290° C. for 8 hours.

The resulting formed article was evaluated as described below.

(1) Heat Resistance

The formed article was exposed to an atmospheric environment at 330° C. for 16 hours to measure the weight reduction ratio, and a change in the external appearance of the formed article was observed. The results are listed in Table 1.

(2) Weight Swelling Change Ratio (Vapor Resistance Test)

The weight swelling change ratio was measured as described below, and a change in external appearance due to the vapor resistance test was observed. The results are listed in Table 2.

(i) Measurement of Weight Swelling Ratio

The weight swelling ratio of a strip-shaped formed article (length: 20 mm, width: 10 mm, thickness: 1 mm) before being subjected to the vapor resistance test (300° C.) was measured as described below.

Specifically, the formed article was immersed in a perfluorocarbon solution (Fluorinert FC-3283 (manufactured by 3M Japan Limited)) at room temperature (21 to 25° C.) for 72 hours, and the weight swelling ratio due to immersion was calculated using the following expression.

Weight swelling ratio (%)=((weight after immersion)−(weight before immersion))/(weight before immersion)×100

(ii) Vapor Resistance Test (300° C.)

The formed article was then subjected to the vapor resistance test (300° C.).

Specifically, the formed article was exposed to saturated water vapor at 300° C. for 22 hours.

(iii) Measurement of Weight Swelling Ratio after Vapor Resistance Test (300° C.)

The formed article that had been subjected to the vapor resistance test (300° C.) was immersed in a perfluorocarbon solution (Fluorinert FC-3283 (manufactured by 3M Japan Limited)) at room temperature (21 to 25° C.) for 72 hours, and the weight swelling ratio of the formed article after the vapor resistance test (300° C.) was measured as described above.

The change ratio (%) with respect to the weight swelling ratio due to the vapor resistance test (300° C.) was calculated using the weight swelling ratio before the vapor resistance test and the weight swelling ratio after the vapor resistance test (see the following expression).

Change ratio (%)=((weight swelling ratio after vapor resistance test)−(weight swelling ratio before vapor resistance test))/(weight swelling ratio before vapor resistance test)×100

Example 2

Synthesis of Compound 2

A compound 2 was synthesized as described below.

A 2 L four-necked flask equipped with a stirrer was charged with 4,4'-biphenyldicarbaldehyde (63.3 g, 0.30 mol), a zinc powder (59.2 g, 0.90 mol), triphenylphosphine (315.8 g, 1.20 mol), and N,N-dimethylacetamide (600 mL). Difluorodibromomethane (221.2 g, 1.05 mol) was slowly added to the mixture at room temperature to 40° C. with stirring. After stirring the mixture at room temperature overnight, the mixture was subjected to extraction using hexane (1 L, 3 times), and the hexane layer was washed with a 20% sodium chloride solution (200 mL, 3 times), dried over anhydrous magnesium sulfate, and concentrated under reduced pressure. The resulting concentrate was purified by silica gel chromatography to obtain 33.5 g of 4,4'-bis(2,2-difluorovinyl)biphenyl (compound 2) (white solid) (isolated yield: 40%).

(Compound 2)

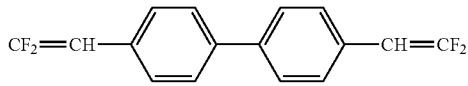

The melting point of the compound 2 was 88 to 90° C. The compound 2 was subjected to GC-MS, $^1$H-NMR, and $^{19}$F-NMR analysis in the same manner as in Example 1. The results are listed below.

GC-MS (m/z): 278 (M$^+$), 256, 227, 207, 139, 89
$^1$H-NMR (Acetone-d$_6$, 400 MHz); 5.30 ppm (dd, 2H), 7.38 ppm (d, 4H, Ar—H), 7.55 ppm (d, 4H, Ar—H)
$^{19}$F-NMR (Acetone-d$_6$, 376 MHz); −84.3 ppm (d, 2F), −82.4 ppm (dd, 2F)

Evaluation of Compound 2

A composition and a formed article were prepared in the same manner as in Example 1, except that the compound 2 was used as the crosslinking agent instead of the compound 1, and the formed article was evaluated in the same manner as in Example 1. The results are listed in Tables 1 and 2.

Example 3

Evaluation of Compound 3

A compound 3 was synthesized as described below.

A 50 mL four-necked flask equipped with a stirrer was charged with zinc chloride (1.57 g, 11.5 mmol) and tetrahydrofuran (20 mL) in a nitrogen atmosphere. After the addition of 1,1,1,3-tetrafluoroethane (1.78 g, 17.4 mmol) at −20° C., a solution prepared by dissolving lithium diisopropylamide in n-hexane and tetrahydrofuran (1.0 M, 21.4 mL, 23.4 mmol) was added dropwise to the mixture. After the addition of 4,4'-diiodobiphenyl (1.33 g, 3.3 mmol) and tetrakis(triphenylphosphine)palladium (0.13 g, 0.11 mmol), the resulting mixture was stirred at room temperature overnight. After evaporating the solvent, the resulting concentrate was subjected to a silica gel treatment to obtain a reaction mixture.

A 25 mL three-necked flask equipped with a stirrer was charged with the reaction mixture and tetrahydrofuran (10 mL). A solution prepared by dissolving sodium bis(2-methoxyethoxy)aluminum hydride in toluene (1.21 g, 4.2 mmol, concentration: about 70%) was slowly added dropwise to the mixture at 0 to 5° C. with stirring. After stirring the mixture at room temperature overnight, the reaction was quenched using a hydrochloric acid aqueous solution, and a concentrate obtained by performing an ordinary post-treatment operation was purified by silica gel chromatography to obtain 0.49 g of 4,4'-bis(1,2-difluorovinyl)biphenyl (compound 3) (white solid) (isolated yield: 54%).

(Compound 3)

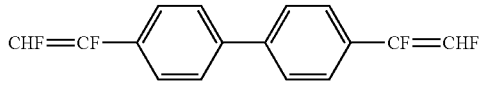

The melting point of the compound 3 was 123 to 128° C. The compound 3 was subjected to GC-MS, $^1$H-NMR, and $^{19}$F-NMR analysis in the same manner as in Example 1. The results are listed below. It was found that the compound 3 was a mixture including three isomers (E-E, E-Z, and Z-Z). The ratio (E-E:E-Z:Z-Z) of these isomers was 34:48:18.

GC-MS (m/z): 278 (M$^+$), 256, 238, 139, 75, 61, 45

(E-E)

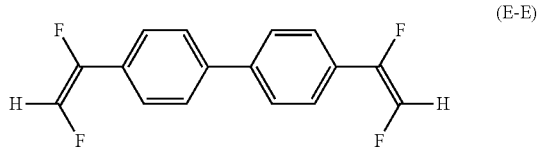 [SMILES: F/C=C(/F)c1ccc(-c2ccc(/C(F)=C\F)cc2)cc1]

$^1$H-NMR (Acetone-d$_6$, 400 MHz); 7.72 ppm (dd, 2H), 7.75 ppm (d, 4H, Ar—H), 7.85 ppm (d, 4H, Ar—H)
$^{19}$F-NMR (Acetone-d$_6$, 376 MHz); −173.8 ppm (ddd, 2F), −167.5 ppm (dd, 2F)

(E-Z)

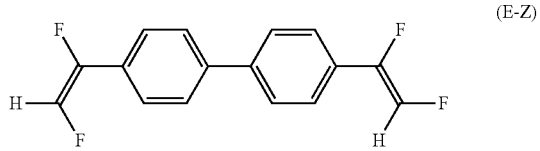

$^1$H-NMR (Acetone-d$_6$, 400 MHz); 7.48 ppm (dd, 1H), 7.62 ppm (d, 2H, Ar—H), 7.70 ppm (dd, 1H), 7.72-7.85 ppm (m, 6H, Ar—H)
$^{19}$F-NMR (Acetone-d$_6$, 376 MHz); −173.8 ppm (ddd, 1F), −167.5 ppm (dd, 1F), −164.8 ppm (dd, 1F), −145.1 ppm (d, 1F)

(Z-Z)

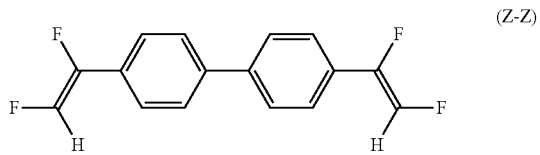 [SMILES: F/C=C(\F)c1ccc(-c2ccc(/C(F)=C/F)cc2)cc1]

$^1$H-NMR (Acetone-d$_6$, 400 MHz); 7.43 ppm (dd, 2H), 7.47 ppm (d, 4H, Ar—H), 7.62 ppm (d, 4H, Ar—H)
$^{19}$F-NMR (Acetone-d$_6$, 376 MHz); −164.9 ppm (dd, 2F), −145.1 ppm (d, 2F)

Evaluation of Compound 3

A composition and a formed article were prepared in the same manner as in Example 1, except that the compound 3 was used as the crosslinking agent instead of the compound 1, and the formed article was evaluated in the same manner as in Example 1. The results are listed in Tables 1 and 2.

Example 4

Synthesis of Compound 4

A compound 4 was synthesized as described below.

A 200 mL four-necked flask equipped with a stirrer was charged with tetrahydrofuran (50 mL) and 1,1,1,2-tetrafluoroethane (4.77 g, 46.8 mmol) in a nitrogen atmosphere. A solution prepared by dissolving n-butyllithium in n-hexane (1.6 M, 50 mL, 80.7 mmol) was slowly added dropwise to the mixture at −78° C., and a solution (50 mL) prepared by dissolving 4,4'-biphenyldicarbaldehyde (2.43 g, 11.5 mmol)

in tetrahydrofuran was added dropwise to the resulting mixture. After the addition of water (0.5 mL) at 0° C., the solvent was evaporated to obtain a reaction mixture.

A 500 mL Teflon (registered trademark) reactor equipped with a stirrer was charged with chloroform (45 mL) and pyridinium poly(hydrogen fluoride) (38.5 g, 103.9 mmol). A solution (40 mL) prepared by dissolving the reaction mixture in chloroform was slowly added dropwise to the mixture at 0 to 5° C. with stirring. After stirring the mixture at room temperature for 3 hours, the mixture was neutralized using a sodium hydrogen carbonate aqueous solution. The organic layer was concentrated under reduced pressure, and the concentrate was purified by silica gel chromatography to obtain 3.65 g of 4,4'-bis(2-trifluoromethyl-2-fluorovinyl) biphenyl (compound 4) (white solid) (isolated yield: 84%).

(Compound 4)

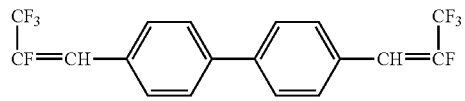

The melting point of the compound 4 was 156 to 158° C. The compound 4 was subjected to GC-MS, $^1$H-NMR, and $^{19}$F-NMR analysis in the same manner as in Example 1. The results are listed below.

GC-MS (m/z): 374 (M$^+$), 354, 295, 263, 227, 155, 111, 109, 91

$^1$H-NMR (Acetone-d$_6$, 400 MHz); 6.84 ppm (d, 2H), 7.80 ppm (d, 4H, Ar—H), 7.83 ppm (d, 4H, Ar—H)

$^{19}$F-NMR (Acetone-d$_6$, 376 MHz); −132.2 ppm (ddd, 2F), −70.5 ppm (d, 6F, CF$_3$)

Evaluation of Compound 4

A composition and a formed article were prepared in the same manner as in Example 1, except that the compound 4 was used as the crosslinking agent instead of the compound 1, and the formed article was evaluated in the same manner as in Example 1. The results are listed in Tables 1 and 2.

Example 5

Synthesis of Compound 5

A compound 5 was synthesized as described below.

A 500 mL four-necked flask equipped with a stirrer was charged with 1,6-bis(4-bromophenyl)-1,1,2,2,3,3,4,4,5,5,6,6-dodecafluorohexane (11.51 g, 18.8 mmol) and tetrahydrofuran (370 mL) in a nitrogen atmosphere. A solution prepared by dissolving n-butyllithium in n-hexane (1.6 M, 26.0 mL, 41.4 mmol) was slowly added dropwise to the mixture at −78° C. with stirring. Next, N,N-dimethylformamide (4.01 g, 54.9 mmol) was slowly added dropwise to the mixture, and the resulting mixture was heated to 0° C. After the addition of a hydrochloric acid aqueous solution, the organic layer was washed with a 20% sodium chloride solution (100 mL, 3 times), dried over anhydrous magnesium sulfate, and concentrated under reduced pressure to obtain 8.00 g of 1,6-bis(4-formylphenyl)-1,1,2,2,3,3,4,4,5,5,6,6-dodecafluorohexane (light yellow solid).

A 200 mL four-necked flask equipped with a stirrer was charged with 1,6-bis(4-formylphenyl)-1,1,2,2,3,3,4,4,5,5,6,6-dodecafluorohexane (5.11 g, 10.0 mmol), a zinc powder (1.96 g, 30.0 mmol), triphenylphosphine (10.49 g, 40.0 mmol) and N,N-dimethylacetamide (40 mL) in a nitrogen atmosphere. A solution (10 mL) prepared by dissolving difluorodibromomethane (7.34 g, 35.0 mmol) in N,N-dimethylacetamide was slowly added dropwise to the mixture at room temperature to 40° C. with stirring, and the resulting mixture was stirred at room temperature overnight. After the addition of hexane (100 mL), a solid precipitate was separated by filtration. The filtrate was washed with a 20% sodium chloride solution (50 mL, 3 times), dried over anhydrous magnesium sulfate, and concentrated under reduced pressure. The resulting concentrate was purified by silica gel chromatography to obtain 1.73 g of 1,6-bis[4-(2,2-difluorovinyl)phenyl]-1,1,2,2,3,3,4,4,5,5,6,6-dodecafluorohexane (compound 5) (white solid) (isolated yield: 26%).

(Compound 5)

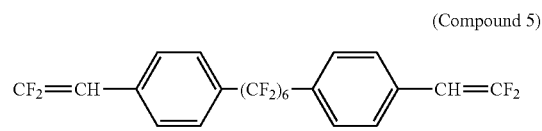

The melting point of the compound 5 was 68 to 70° C. The compound 5 was subjected to GC-MS, $^1$H-NMR, and $^{19}$F-NMR analysis in the same manner as in Example 1. The results are listed below.

GC-MS (m/z): 578 (M$^+$), 559, 220, 189, 169, 138, 119, 99

$^1$H-NMR (Acetone-d$_6$, 400 MHz); 5.77 ppm (dd, 2H), 7.64 ppm (d, 4H, Ar—H), 7.69 ppm (d, 4H, Ar—H)

$^{19}$F-NMR (Acetone-d$_6$, 376 MHz); −121.7 ppm (s, 4F, CF$_2$), −121.2 ppm (s, 4F, CF$_2$), −110.3 ppm (s, 4F, CF$_2$), −82.7 ppm (d, 2F), −80.9 ppm (dd, 2F)

Evaluation of Compound 5

A composition and a formed article were prepared in the same manner as in Example 1, except that the compound 5 was used as the crosslinking agent instead of the compound 1, and the formed article was evaluated in the same manner as in Example 1. The results are listed in Tables 1 and 2.

Example 6

Synthesis of Compound 6

A compound 6 was synthesized as described below.

Specifically, reactions were effected in the same manner as in Example 2, except that 3,3'-biphenyldicarbaldehyde was used instead of 4,4'-biphenyldicarbaldehyde, to synthesize 3,3'-bis(2,2-difluorovinyl)biphenyl (compound 6). The compound 6 was obtained in the form of a light yellow solid, and the isolated yield was 36%.

(Compound 6)

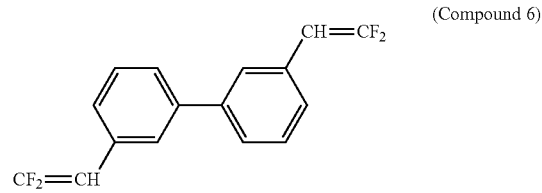

The melting point of the compound 6 was 29 to 30° C. The compound 6 was subjected to GC-MS, $^1$H-NMR, and $^{19}$F-NMR analysis in the same manner as in Example 1. The results are listed below.

GC-MS (m/z): 278 (M$^+$), 256, 227, 207, 139, 89

$^1$H-NMR (Acetone-d$_6$, 400 MHz); 5.68 ppm (dd, 2H), 7.40-7.68 ppm (m, 8H, Ar—H)

$^{19}$F-NMR (Acetone-d$_6$, 376 MHz); −86.5 ppm (d, 2F), −83.5 ppm (dd, 2F)

Evaluation of Compound 6

A composition and a formed article were prepared in the same manner as in Example 1, except that the compound 6 was used as the crosslinking agent instead of the compound 1, and the formed article was evaluated in the same manner as in Example 1. The results are listed in Tables 1 and 2.

Example 7

Synthesis of Compound 7

A compound 7 was synthesized as described below.

Specifically, reactions were effected in the same manner as in Example 2, except that 4,4'-diformyl diphenyl ether was used instead of 4,4'-biphenyldicarbaldehyde, to synthesize 4,4'-bis(2,2-difluorovinyl)diphenyl ether (compound 7). The compound 7 was obtained in the form of a white solid, and the isolated yield was 35%.

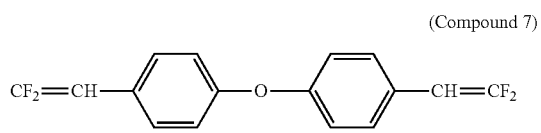
(Compound 7)

The melting point of the compound 7 was 36 to 38° C. The compound 7 was subjected to GC-MS, $^1$H-NMR, and $^{19}$F-NMR analysis in the same manner as in Example 1. The results are listed below.

GC-MS (m/z): 294 (M$^+$), 265, 245, 196, 156, 127, 119, 99

$^1$H-NMR (Acetone-d$_6$, 400 MHz); 5.60 ppm (dd, 2H), 7.04 ppm (d, 4H, Ar—H), 7.43 ppm (d, 4H, Ar—H)

$^{19}$F-NMR (Acetone-d$_6$, 376 MHz); −86.9 ppm (d, 2F), −85.1 ppm (dd, 2F)

Evaluation of Compound 7

A composition and a formed article were prepared in the same manner as in Example 1, except that the compound 7 was used as the crosslinking agent instead of the compound 1, and the formed article was evaluated in the same manner as in Example 1. The results are listed in Tables 1 and 2.

Example 8

Synthesis of Compound 8

A compound 8 was synthesized as described below.

Specifically, reactions were effected in the same manner as in Example 5, except that 1,6-bis(3-bromophenyl)-1,1,2,2,3,3,4,4,5,5,6,6-dodecafluorohexane was used instead of 1,6-bis(4-bromophenyl)-1,1,2,2,3,3,4,4,5,5,6,6-dodecafluorohexane, to synthesize 1,6-bis[3-(2,2-difluorovinyl)phenyl]-1,1,2,2,3,3,4,4,5,5,6,6-dodecafluorohexane (compound 8). The compound 8 was obtained in the form of a white solid, and the isolated yield was 22%.

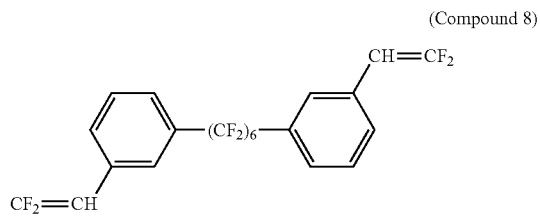
(Compound 8)

The melting point of the compound 8 was 23 to 25° C. The compound 8 was subjected to GC-MS, $^1$H-NMR, and $^{19}$F-NMR analysis in the same manner as in Example 1. The results are listed below.

GC-MS (m/z): 578 (M$^+$), 559, 220, 189, 169, 138, 119, 99

$^1$H-NMR (Acetone-d$_6$, 400 MHz); 5.79 ppm (dd, 2H), 7.57-7.74 ppm (m, 8H, Ar—H)

$^{19}$F-NMR (Acetone-d$_6$, 376 MHz); −121.7 ppm (s, 4F, CF$_2$), −121.1 ppm (s, 4F, CF$_2$), −110.5 ppm (s, 4F, CF$_2$), −83.9 ppm (d, 2F), −82.3 ppm (dd, 2F)

Evaluation of Compound 8

A composition and a formed article were prepared in the same manner as in Example 1, except that the compound 8 was used as the crosslinking agent instead of the compound 1, and the formed article was evaluated in the same manner as in Example 1. The results are listed in Tables 1 and 2.

Example 9

Synthesis of Compound 9

A compound 9 was synthesized as described below.

A 500 mL four-necked flask equipped with a stirrer was charged with 1,4-bis(4-bromophenyl)-1,1,2,2,3,3,4,4-octafluorobutane (10.24 g, 20.0 mmol) and tetrahydrofuran (350 mL) in a nitrogen atmosphere. A solution prepared by dissolving n-butyllithium in n-hexane (1.6 M, 25.6 mL, 41 mmol) was slowly added dropwise to the mixture at −78° C. with stirring. Next, N,N-dimethylformamide (4.39 g, 60.0 mmol) was slowly added dropwise to the mixture, and the resulting mixture was heated to 0° C. After the addition of a hydrochloric acid aqueous solution, the organic layer was washed with a 20% sodium chloride solution (100 mL, 3 times), dried over anhydrous magnesium sulfate, and concentrated under reduced pressure to obtain 4.99 g of 1,4-bis(4-formylphenyl)-1,1,2,2,3,3,4,4-octafluorobutane (light yellow solid).

A 300 mL four-necked flask equipped with a stirrer was charged with 1,4-bis(4-formylphenyl)-1,1,2,2,3,3,4,4-octafluorobutane (4.92 g, 12.0 mmol), a zinc powder (2.35 g, 36.0 mmol), triphenylphosphine (12.59 g, 48.0 mmol), and N,N-dimethylacetamide (75 mL) in a nitrogen atmosphere. A solution (20 mL) prepared by dissolving difluorodibromomethane (8.98 g, 42.8 mmol) in N,N-dimethylacetamide was slowly added dropwise to the mixture at room temperature to 40° C. with stirring, and the resulting mixture was stirred at room temperature overnight. After the addition of hexane (150 mL), a solid precipitate was separated by filtration. The filtrate was washed with a 15% sodium chloride solution (50 mL, 3 times), dried over anhydrous magnesium sulfate, and concentrated under reduced pressure. The resulting concentrate was purified by silica gel chromatography to obtain 2.12 g of 1,4-bis[4-(2,2-difluorovinyl)phenyl]-1,1,2,2,3,3,4,4-octafluorobutane (compound 9) (white solid) (isolated yield: 22%).

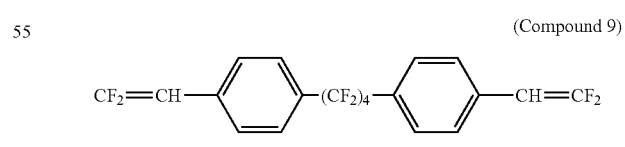
(Compound 9)

The melting point of the compound 9 was 86 to 88° C. The compound 9 was subjected to GC-MS, $^1$H-NMR, and $^{19}$F-NMR analysis in the same manner as in Example 1. The results are listed below.

GC-MS (m/z): 478 (M$^+$), 319, 189, 169, 138, 119, 99

$^1$H-NMR (Acetone-d$_6$, 400 MHz); 5.75 ppm (dd, 2H), 7.62 ppm (d, 4H, Ar—H), 7.66 ppm (d, 4H, Ar—H)

$^{19}$F-NMR (Acetone-d$_6$, 376 MHz); −121.2 ppm (s, 4F, CF$_2$), −110.3 ppm (s, 4F, CF$_2$), −82.9 ppm (d, 2F), −81.1 ppm (dd, 2F)

Comparative Example 1

1,6-Divinyl(perfluorohexane) (manufactured by TOSOH F-TECH, INC.) (see below) was used as a comparative compound 1.

  (Comparative compound 1)

Evaluation of Comparative Compound 1

A composition and a formed article were prepared in the same manner as in Example 1, except that the comparative compound 1 was used as the crosslinking agent instead of the compound 1, and the formed article was evaluated in the same manner as in Example 1. The results are listed in Tables 1 and 2.

TABLE 1

| | Heat resistance | |
| --- | --- | --- |
| | Weight reduction ratio (%) | External appearance |
| Example 1 | 4.6 | Slightly dissolved |
| Example 2 | 2.6 | No change was observed |
| Example 3 | 2.8 | No change was observed |
| Example 4 | 4.9 | No change was observed |
| Example 5 | 2.3 | No change was observed |
| Example 6 | 0.9 | No change was observed |
| Example 7 | 0.9 | No change was observed |
| Example 8 | 1.4 | No change was observed |
| Comparative Example 1 | 9.5 | Dissolved |

TABLE 2

| | Weight swelling ratio (%) | | | |
| --- | --- | --- | --- | --- |
| | Before vapor resistance test | After vapor resistance test | Change ratio (%) | External appearance |
| Example 1 | 324 | 417 | 29 | No change was observed |
| Example 2 | 139 | 209 | 50 | No change was observed |
| Example 3 | 251 | 522 | 108 | No change was observed |
| Example 4 | 307 | 541 | 76 | No change was observed |
| Example 5 | 171 | 251 | 47 | No change was observed |
| Example 6 | 156 | 261 | 67 | No change was observed |
| Example 7 | 147 | 217 | 48 | No change was observed |
| Example 8 | 201 | 315 | 57 | No change was observed |
| Comparative Example 1 | 142 | 253 | 78 | No change was observed |

INDUSTRIAL APPLICABILITY

The fluorine-containing aromatic compound or the crosslinking agent according to the invention can be used as a crosslinking agent for a fluoroelastomer. The crosslinked fluoroelastomer according to the invention can be used as a seal material for which heat resistance is required.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the description and the specification of the Japanese application on the basis of which the present application claims Paris Convention priority are incorporated herein by reference in its entirety.

The invention claimed is:

1. A composition comprising a fluoroelastomer, a crosslinking initiator, and a crosslinking agent, wherein the crosslinking agent comprises a compound represented by a formula (4),

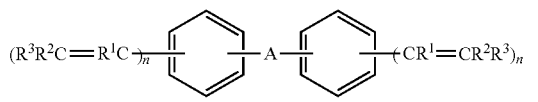

(4)

wherein A is a single bond, —O—, —S—, a heteroatom-containing group, a linear or a branched alkylene group, a cycloalkylene group, or an arylene group and these groups may be fluorinated partially or completely; R$^1$, R$^2$, and R$^3$ are independently a hydrogen atom, a fluorine atom, an alkyl group, a fluoroalkyl group, or a substituted or unsubstituted aryl group, a plurality of R$^1$ are identical to or different from each other, a plurality of R$^2$ are identical to or different from each other, and a plurality of R$^3$ are identical to or different from each other, provided that in each —CR$^1$=CR$^2$R$^3$, at least one of R$^1$, R$^2$, and R$^3$ is a hydrogen and at least one of R$^1$, R$^2$, and R$^3$ is a fluorine atom or a fluorine atom-containing group; n are independently an integer from 1 to 5; and each hydrogen on the benzene rings may be substituted.

2. The composition according to claim 1, comprising the crosslinking agent in an amount of 0.5 to 30 mmol based on 100 g of the fluoroelastomer.

3. The composition according to claim 1, comprising the crosslinking initiator in an amount of 0.3 to 15 mmol based on 100 g of the fluoroelastomer.

4. A crosslinked fluoroelastomer obtained by crosslinking the composition according to claim 1.

5. The crosslinked fluoroelastomer according to claim 4, having a change ratio of 70% or less with respect to a weight swelling ratio when exposed to saturated water vapor at 300° C. for 22 hours, the weight swelling ratio being measured after immersing the crosslinked fluoroelastomer in a perfluorocarbon solution at 21 to 25° C. for 72 hours.

6. The crosslinked fluoroelastomer according to claim 4, having a weight reduction ratio of 7% or less when exposed to an atmospheric environment at 330° C. for 16 hours.

7. A formed article comprising the crosslinked fluoroelastomer according to claim 4.

8. The formed article according to claim 7, the formed article being a seal material.

* * * * *